United States Patent [19]

Davis et al.

[11] Patent Number: 4,536,713

[45] Date of Patent: Aug. 20, 1985

[54] ELECTRICAL RESISTIVITY MEASUREMENT OF A FLOWING DRILLING FLUID USING EDDY CURRENTS GENERATED THEREIN

[75] Inventors: Mark H. Davis; Richard A. Meador, both of Spring, Tex.; Macmillan M. Wisler, Lafayette, La.

[73] Assignee: NL Industries, Inc., New York, N.Y.

[21] Appl. No.: 471,879

[22] Filed: Mar. 3, 1983

[51] Int. Cl.³ .................. G01V 3/26; G01N 27/74; E21B 49/00

[52] U.S. Cl. ..................... 324/324; 73/153; 166/250; 175/40; 324/204; 324/346; 324/442

[58] Field of Search ........... 324/204, 324, 325, 333, 324/346, 356, 369, 442; 73/153, 155; 166/65 M, 250, 254; 175/40, 50

[56] References Cited

U.S. PATENT DOCUMENTS

| | | | |
|---|---|---|---|
| 2,411,696 | 11/1946 | Silverman et al. | 324/369 X |
| 2,948,847 | 5/1957 | Bravenec et al. | |
| 3,059,695 | 10/1962 | Barry et al. | 324/324 X |
| 3,388,323 | 6/1968 | Stripling | 324/333 |
| 3,701,006 | 10/1972 | Volkel et al. | |
| 3,714,555 | 1/1973 | Greer | |
| 3,720,870 | 3/1973 | Sueda | |
| 3,987,362 | 10/1976 | McCann et al. | |
| 4,019,126 | 4/1977 | Meador | 324/333 |
| 4,100,491 | 7/1978 | Newman et al. | 324/204 |
| 4,134,059 | 1/1979 | Stankoff | |

FOREIGN PATENT DOCUMENTS 2029580  3/1980  United Kingdom ............ 324/204

*Primary Examiner*—Gerard R. Strecker
*Attorney, Agent, or Firm*—Browning, Bushman, Zamecki & Anderson

[57] ABSTRACT

A high permeability ferrite core, which includes a gap between adjacent ends thereof, is combined with a magnetic coil encircling the core, and is located in a sub positioned in the drill string just above the drill bit of a borehole drilling rig. The core is positioned so that the gap thereof lies across a recess region formed in the outer wall of the sub. Drilling fluids flow along the outer surface of the sub on the return path from the drill bit to the mud pits located at the surface of the borehole. A constant current, or voltage, at a frequency within the range of 20 KHz–20 MHz is applied to the terminals of the coil encircling the core and the eddy currents developed in the gap region produce a measurable back emf at the coil terminals. The current produced by this emf voltage is indicative of the resistivity of the drilling fluid within the recess region in the wall of the sub and the fluctuations of the voltage accurately follow the variations in drilling fluid resistivity.

25 Claims, 4 Drawing Figures

ELECTRICAL RESISTIVITY MEASUREMENT OF A FLOWING DRILLING FLUID USING EDDY CURRENTS GENERATED THEREIN

BACKGROUND OF THE INVENTION

1. Field of the Invention

The present invention relates to systems for measuring the resistivity of fluids, and more particularly, to an eddy-current type probe for downhole measurement of drilling fluid resistivity and variations therein. The invention is particularly suited for measurement while drilling applications.

2. Description of the Background

In the drilling of boreholes for oil and gas wells, it is customary that the borehole be filled with a supply of drilled mud to maintain pressure control over the various earth formations through which the borehole passes. During the drilling operation drilling mud is continuously circulated between the surface and the bottom of the borehole in order to cool the drill bit and to carry away cuttings as they are removed from the earth formations by the drill bit. Drilling mud is pushed down the axial opening in the drill pipe, out openings in the drill bit and back up the borehole towards the surface through the annular space between the outside of the drill string and the walls of the borehole.

As huge quantities of drilling mud pass the drilling bit, the chemical and physical properties of the drilling mud are often changed. For example, should the drilling bit be penetrating an earth formation which contains a substantial quantity of salt water, an influx of such connate fluids into the borehole will produce a corresponding increase in the salinity of the drilling mud and a corresponding decrease in the electrical resistivity of that mud. Further, as the drill bit penetrates a fluid permeable formation having little or no connate water contained therein, water from the mud will be carried into the formation and the solid particles carried in suspension within the drilling mud will be caked onto the walls of the formation. As a result of this phenomenon there will be a net loss of chloride ions from the associated portions of the drilling mud which will cause a corresponding increase in the electrical resistivity of the mud due to a decrease in its salinity.

It is noted that there is very little net change in the resistivity of the drilling fluid except that which occurs very near the drilling bit. Thus, measurement or continuous monitoring of the resistivity of the drilling fluids at or near the drilling bit will produce data which is indicative of characteristics of the formation through which the drilling bit is at that time passing.

Prior systems have generally made drilling mud resistivity measurements only at the surface. Further, prior techniques have made comparative measurements wherein the differences between the resistivity of the drilling fluids flowing out of the borehole are correlated in an effort to log the characteristics of the formations through which the drilling bit has passed. It is to be noted, however, that if measurements are only made at the surface, e.g., at the returning drilling fluids reservoir, there will have been a substantial time delay between the passage of the drilling bit through the formation and the measurement of the changed resistivity of the drilling mud associated with its passage through that particular formation. Thus, in order to enable the use of drilling fluid resistivity measurements to provide an accurate, real time indication of the physical characteristics of the formation through which the bit is passing during the drilling operation, the measurements must be made at or near the drilling bit and instantly monitored therefrom. This is a very difficult undertaking for most of the prior techniques of drilling fluids resistivity measurements.

Most prior drilling fluid resistivity monitoring systems for use down hole have employed either a two electrode configuration or a four electrode configuration. In the two electrode systems, current is induced to flow between two spaced apart electrodes between which is positioned the fluid, the resistivity of which is to be measured. Although the current flow between the two electrodes is indicative of the resistivity of the fluid therebetween, it is noted that this same current flow produces a polarization of those electrodes and thereby inhibits an accurate measurement of the resistivity of the fluid.

In the four electrode system, two electrodes are used for stimulation of electric current in the fluid medium and two electrodes are used mainly for monitoring the potential difference across the fluid medium. That is, the measuring electrodes draw no current and, therefore, there is no polarization inherent in their operation as in the case of two electrode systems. The principle problem inherent in a four electrode system is the difficulty of measurement of the resistance of very small volumes of fluids with the necessary accuracy. For example, in a measuring while drilling application of the present invention, mud resistivity variation will often occur only in a very narrow volume of space positioned between the outside of the drill collar and the wall of the formation, that is, within a distance typically on the order of three quarters of an inch. Resistivity measurement of such small fluid volumes is beyond the capability of prior four electrode systems.

The system of the present invention overcomes many of the disadvantages of the prior systems and provides for the rapid measurement of fluid resistivity at a location near the drilling bit. The system thus facilitates the delivery to the surface of highly accurate, relatively noise-free, real-time signals indicative of the character of the formation being penetrated by the bit. Such real-time information regarding the nature of the formation being penetrated allows the driller to responsively alter the characteristic of the mud when required.

SUMMARY OF THE INVENTION

The present invention provides method and apparatus for measuring the resistivity of flowing fluids during drilling operations. More particularly, one aspect of the invention relates to apparatus adapted for use within a borehole and comprising a housing disposed within the drill pipe string of a borehole drilling rig. The housing is formed with a sensor region in the outer surface. The sensor region includes a pair of opposed wall portions adapted to be substantially and continuously filled by drilling fluids flowing along the outer surface of the housing. A high permeability magnetic core having a pair of opposed ends forming a gap region therebetween is positioned within the housing. The respective core ends are positioned adjacent to the opposed wall portions of the sensor region to position the sensor region within the gap of the core. Means are provided for producing an alternating, electromagnetic flux field of a substantially constant magnitude in the core and the gap region to induce eddy currents in the fluid flowing through the sensor region. Means are also provided for generating a signal proportional to the fluctuations in the elecromagnetic flux field in the core to measure the electrical conductivity of fluids flowing along the outer surface of the housing.

In another aspect, the invention includes a method for measuring the electrical resistivity of fluids flowing within a borehole in a drilling operation. The method comprises the steps of providing a sub having a recess region formed in the outer surface thereof and adapted for coupling to a drill pipe string of a borehole drilling rig. The recess region of the sub comprises a pair of opposed, planar walls and is adapted to be substantially and continuously filled by fluids. The sub is positioned in the drill string and within the borehole relative to the drilling bit. Fluids then flow within the recess of the sub for measuring the electrical resistivity of the fluids. An alternating, electromagnetic flux field of a substantially constant magnitude is then generated within the recess. An output signal is then produced in response to variations in the flux field produced by eddy current flow in the fluids. The output signal is an indication of the resistivity of the fluids in the recess region.

DESCRIPTION OF PREFERRED EMBODIMENTS

Figures 1, 4:
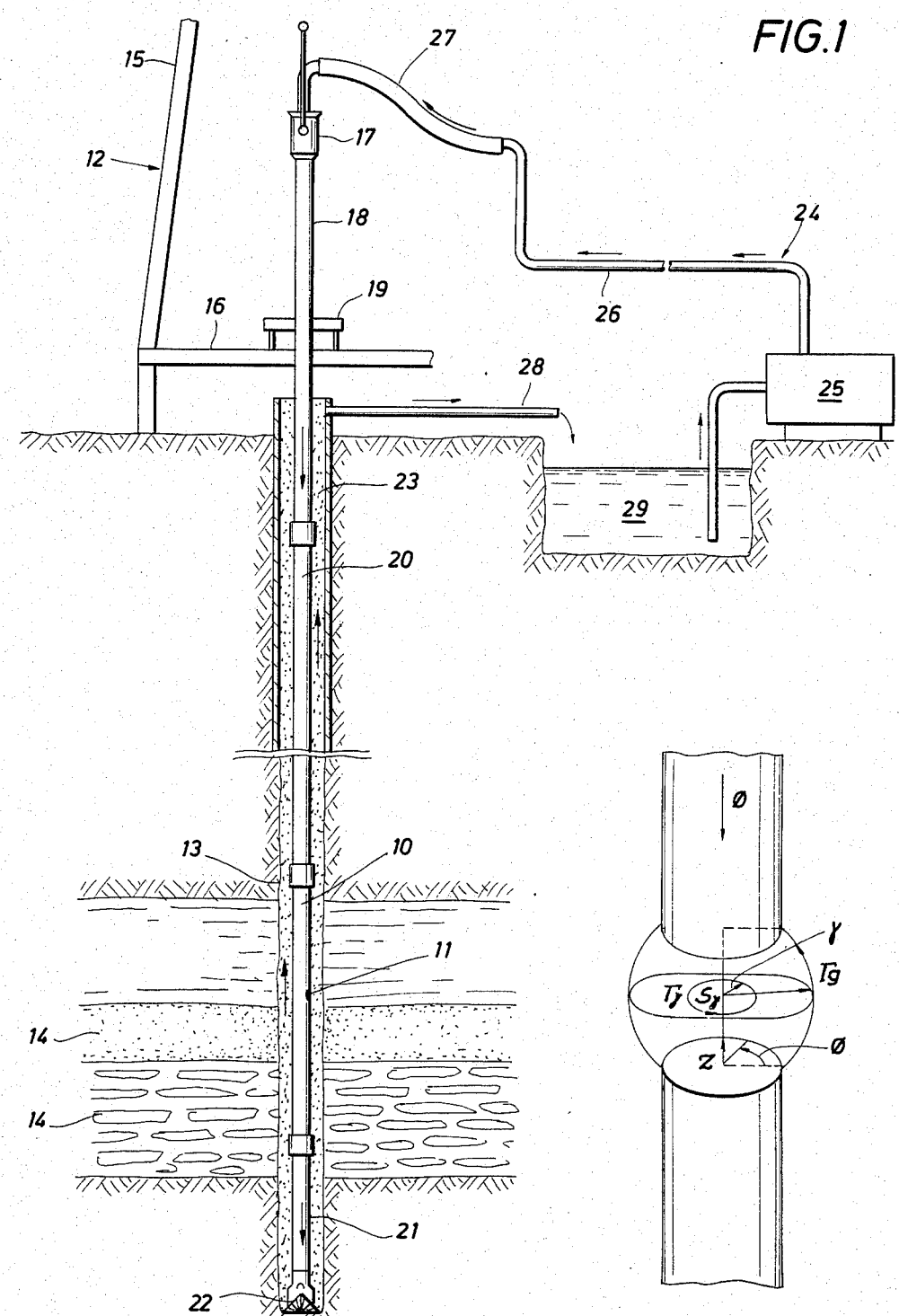
FIG. 1 is a schematic illustration of a portion of a typical rotary drilling rig and associated drilling fluid circulating means including a resistivity measuring system constructed in accordance with the principles of the present invention.
FIG. 4 is a simplified illustrative diagram of a gap region lying between two circular pole pieces, which diagram is useful in analyzing the operation of the present invention.

Referring now to FIG. 1, there is shown a sub 10 incorporating a device 11 constructed in accordance with the teachings of the present invention. The system of the present invention is schematically illustrated in conjunction with conventional rotary drilling apparatus within which drilling fluid, often referred to as drilling "mud," is circulated. A drilling rig 12 is suitably arranged for drilling a borehole 13 through various strata of earth formations 14 to reach subsurface, petrochemical-containing formations. The drilling rig 12 includes a derrick 15 (fragmentally shown) having a drilling floor 16 above which are mounted a draw works and various other pieces of conventional equipment for raising and lowering drilling pipe into the borehole (not shown). The draw works (not shown) is adapted for supporting a swivel 17 from which depends a square shouldered kelly 18 which extends downwardly through a rotary table 19 positioned on the rig floor 16. The rotary drilling table 19 is connected to driving machinery (not shown) and is adapted for rotation of the kelly 18 which supports a depending string of drill pipe 20 and drill collars 21 for carrying a typical rotary drilling bit 22. The housing or sub 10, carrying the resistivity measuring device 11 of the present invention, is included within the drill string 20 preferably near the drill bit 22.

In contemporary drilling technology it is customary that the borehole 13 be filled with a supply of drilling fluid or mud 23 which is continuously circulated down the center of the string of drill pipe 20 and collars 21 and out into a region at the bottom of the borehole where the drilling bit 22 is penetrating the formations 14. See directional arrows in FIG. 1. The mud 23 cools the drill bit 22 and carries off formation cuttings as they are removed by the drill bit. Drilling fluids are circulated from the drilling bit 22 externally of the drill string back up the borehole toward the surface.

The drilling rig 12 of FIG. 1 includes a mud circulation system 24 which comprises a relatively high pressure mud pump 25. The output of the mud pump 25 is connected through piping 26 to a flexible hose 27 which is coupled to the upper end of the swivel 17. Mud passes into the top of the swivel 17 down the kelly 18 and into an axial passageway through the drill string of pipe 20 and collars 21. At the bottom of the borehole 13 the mud flows out of the drill string through openings in the bit 22 and returns to the surface via the annular space between the drill string and the outer walls of the borehole. The returning mud flow passes through a discharge pipe 28 and into a mud pit 29 from which the pump 25 draws mud for circulation through the circulation system 24. The mud in the pit 29 is selectively treated and conditioned with various chemical agents to regulate the various chemical and physical properties of the drilling mud before it re-enters the borehole 13. Thus, it will be appreciated that as the mud pump 25 is operated, the drilling fluid is continuously pumped downwardly through the kelly 18 and the drill string and then discharged from one or more ports in the drilling bit 22 into the bottom of the borehole 13. As the drilling fluid leaves the drilling bit 22, the cuttings being removed from the formations 14 by the bit 22 will be held in suspension by the column of drilling fluid and returned to the surface by way of the annular space defined between the borehole 13 and the drill string.

Figure 2:
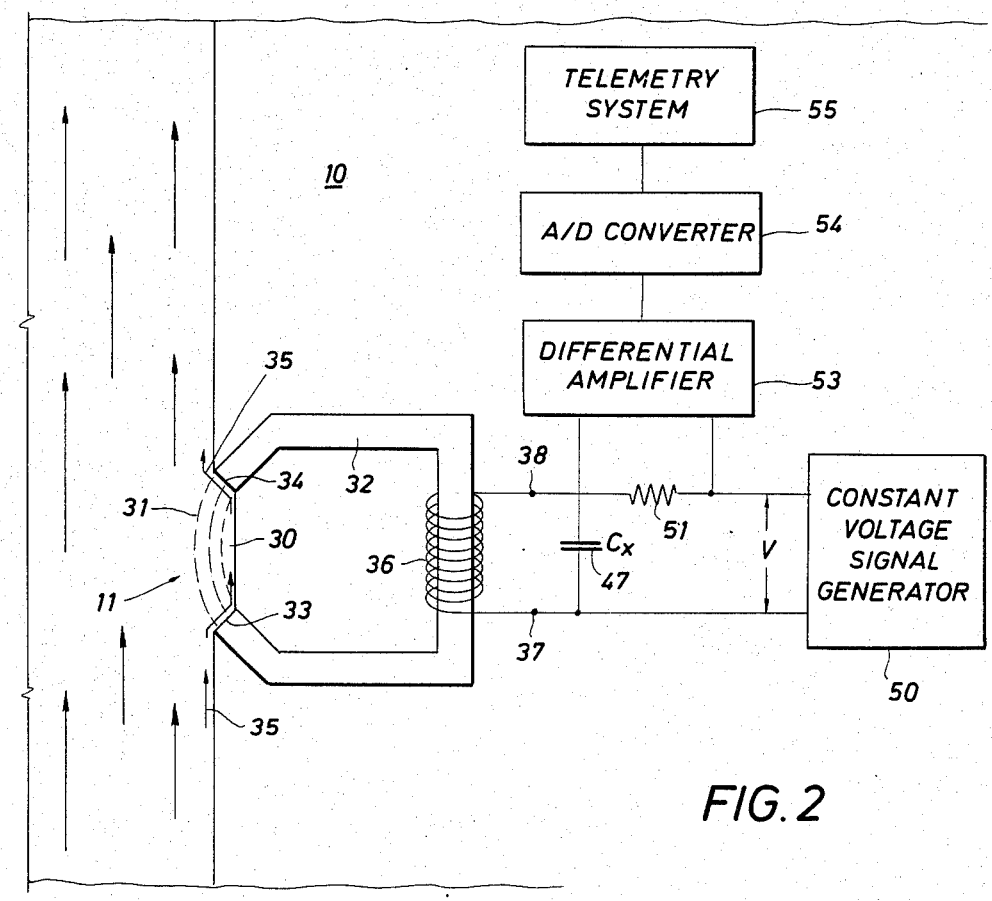
FIG. 2 is a schematic diagram of a resistivity measuring device constructed in accordance with the present invention.

Referring now to FIG. 2, there is shown a schematic diagram of the system of the invention positioned within the upward mud flow path of the borehole. The side wall of the sub 10 containing the system of the present invention includes a small recess region 30 within which an alternating electromagnetic flux field of substantially constant magnitude 31 is developed. A high-permeability ferrite core 32 is positioned so that the ends 33 and 34 of the core form a gap and terminate adjacent opposed planar walls forming the ends of the recess region 30 with the result that the recess is located within the gap. As can be seen, the return fluid flow, denoted by arrows 35, passes adjacent the surface of the sub 10 and continuously and substantially fills the recess region 30 with mud which has just previously been exposed to fluids and particles in the region of the interface of the drill bit 22 with the formation being penetrated. The flat end surfaces 33 and 34 of the ferrite core 32 preferably form the planar end surfaces of the recess 30 and are in direct contact with the fluid flow.

The core 32 is encircled by an exciting coil 36 having a pair of end terminals 37 and 38. A constant current or a constant voltage having a frequency between 20 KHz and 20 MHz is applied to the exciting coil 36 to produce an alternating electromagnetic field 31 in the recess region 30 within the gap between the opposed core end surfaces 33 and 34. Eddy current power losses occur within the gap region of the ferrite core 32 due to the presence of the fluid filling the recess region 30 between the core ends 33 and 34. With a constant voltage input to the coil 36, any change or variation in the fluid conductivity/resistivity will produce a measurable change in the current at terminals 37-38 due to the back emf developed by the eddy current in the fluid. The instrument of the present invention is first calibrated in the laboratory, for example, for cancellation of fluid resistivity as a function current flow, and then, in application, variations in current are used to determine corresponding fluid resistivity changes. Resistivity information is digitized and sent to the surface by conventional borehole telemetry techniques as described further hereinafter.

The mathematical basis for the new and improved system of the present invention will best demonstrate the accuracy which can be obtained by means of the apparatus shown in FIGS. 1 and 2.

Figure 3:
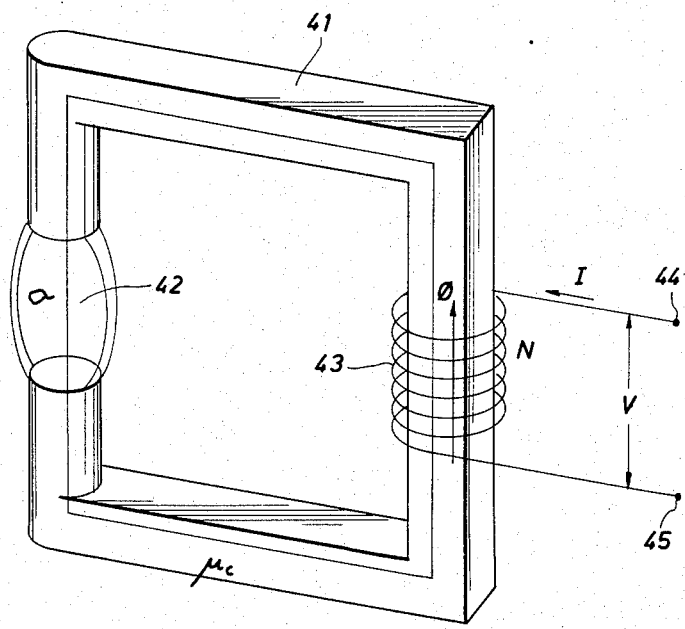
FIG. 3 is a simplified illustrative diagram of the various electrical parameters associated with the operation of the device of FIG. 2.

The principle of operation of the present technique is most clearly illustrated by reference to FIG. 3, wherein there is shown a core 41 comprising a gap 42, and a coil 43 having N turns of wire which is used as a reference for determination of a voltage-current (V-I) relationship. Maxwell's curl H equation, as usually applied to magnetic circuits, is as follows:

$$\nabla \times H = J + \frac{\partial D}{\partial t} \quad (1)$$

In accordance with Ampere's Circuital Law, the $\partial D/\partial t$ term is zero because of either low frequency application or high conductivity current paths such as along conducting wire. However, the term is retained in this analysis so that it will be applicable to wide ranges of frequencies and conductivities within the gap region. With the integration path $\Gamma$ through the center of the core 41 and gap region 42, Stoke's theorem is applied as follows:

$$\int_\Gamma H \cdot d\Gamma = \int_S \left( J + \frac{\partial D}{\partial t} \right) \cdot dS \quad (2)$$

where s is the surface enclosed by $\Gamma$. The left hand side integral is evaluated in the normal manner by assuming the flux $\Phi$ to be constant along the magnetic circuit and assuming the magnetic field B to be uniform. Thus, $$\int_\Gamma H \cdot d\Gamma = \frac{\Phi l_g}{\mu_g A_g} + \frac{\Phi l_c}{\mu_c A_c} \quad (3)$$

where $l_g$, $\mu_g$, $A_g$ and $l_c$, $\mu_c$ and $A_c$ are length, permeability and cross-sectional area of the gap and core, respectively.

The right side of Equation (2) is also evaluated in two parts. Assuming negligible core current condition and considering only the gap region and the current carrying wires, one finds:

$$\int_S \left( J + \frac{\partial D}{\partial t} \right) \cdot dS = NI + \int_{S_g} \left( J + \frac{\partial D}{\partial t} \right) \cdot dS_g \quad (4)$$

The number of turns of wire in the coil, N, times the current I is the contribution of the coil, the surface integral is now applicable only to the gap region. For ease of analysis the gap region may be considered with cylindrical geometry as shown in FIG. 4. The integral on the right side of Equation (4) is a result of the magnetic flux flowing in the gap, and may be rewritten in terms of current only, assuming a harmonic "$e^{i\omega t}$" time dependence. Thus, $$\int_{S_g} \left( J + \frac{\partial D}{\partial t} \right) \cdot dS_g = \int_{S_g} \left( J - \frac{i\omega\epsilon}{\sigma} J \right) \cdot dS_g = \quad (5)$$

$$\left( 1 - \frac{i\omega\epsilon}{\sigma} \right) \int_{S_g} J \cdot dS_g$$

The current through the surface $S_g$ is calculated by using Maxwell's curl E equation and substituting current for E as follows:

$$\nabla \cdot E = -\frac{\partial B}{\partial t} \quad (6)$$

$$\nabla \cdot \frac{J}{\sigma} = i\omega B \quad (7)$$

again assuming a harmonic time factor. Applying Stoke's theorem, this time using the curve $\Gamma_\gamma$ of FIG. 4 where the direction is taken such that positive influx is in a direction normal to the included surface, one obtains:

$$\int_{\Gamma_\gamma} \frac{J}{\sigma} \cdot d\Gamma_\gamma = i\omega \int_{S_\gamma} B \cdot dS_\gamma \quad (8)$$

Consider the curve $\Gamma_\Phi$ to be along the cylindrical $\Phi$ direction, and that B is independent of radial direction and, in particular, that:

$$B = -\hat{z} B_z = -\frac{\Phi}{A_g} = -\frac{\Phi}{\pi a^2} \quad (9)$$

While this term B is not exact for large gap area-to-pole area ratios, an "equivalent" area may be found for a particular geometry. By integrating both sides of Equation (8) one gets:

$$2\pi\gamma \frac{J_\Phi}{\sigma} = \frac{-i\omega\Phi}{a^2} \gamma^2$$

Equation (5) can now be evaluated. Recalling that the positive direction for S is out of the page so that $\Phi \cdot s = -1$, one finds:

$$\left( 1 - \frac{i\omega\epsilon}{\sigma} \right) \int_0^{l_g} dZ \int_0^a (-J\Phi) d\gamma = \quad (11)$$

$$\left( 1 - \frac{i\omega\epsilon}{\sigma} \right) \left( \frac{i\omega\sigma}{2\pi} \Phi \right) \int_0^{l_g} \frac{dZ}{a^2} \int_0^a \gamma d\gamma =$$

$$\left( 1 - \frac{i\omega\epsilon}{\sigma} \right) \left( \frac{i\omega\sigma}{2\pi} \Phi \right) l_g$$

where a is a function of Z in the gap. Equation (2) now becomes:

$$\frac{\Phi l_g}{\mu_g A_g} + \frac{\Phi l}{\mu_c A_c} = NI + \left(1 - \frac{i\omega\epsilon}{\sigma}\right)\left(\frac{i\omega\sigma\Phi l_g}{4\pi}\right) \quad (12)$$

Since in the structure of the present invention a highly permeable core material is utilized, the second term in Equation (12) is negligible compared with the first term for reasonably large gap size, and Equation (12) may be rewritten to obtain:

$$NI = \Phi l_g \left[\frac{l}{\mu_g A_g} - \frac{i\omega\sigma}{4\pi} - \frac{\omega^2 \epsilon}{4\pi}\right] \quad (13)$$

The emf caused by the hanging flux $\Phi$ in the core 41 causes voltage at the terminals of the coil 43. It follows from the curl E equation that back emf will develop at terminals 44 and 45 of the coil 43, as follows:

$$V/N = -i\omega\Phi \quad (14)$$

Rewriting Equation (13) in terms of circuit terminal characteristics one finds:

$$\frac{I}{V} = \frac{l_g}{N^2} \left[\frac{i}{\omega\mu_g A_g} - \frac{i\omega\epsilon}{4\pi} + \frac{\sigma}{4\pi}\right] \quad (15)$$

From Equation (15) it is evident that the admittance of the measurement coil may be modeled as a parallel circuit including an inductance $L = \mu_g A_g$, a capacitance $C = \epsilon/4\pi$, and a resistance $R = 4\pi/\Sigma$.

If a tuning capacitor $C_x$ is added in parallel and adjusted in value such that the circuit is in resonance, that is, $$C_x = \frac{1}{\omega^2 \mu_g A_g} - \frac{\epsilon}{4\pi}, \text{ for } \frac{1}{\omega^2 \mu_g A_g} > \frac{\epsilon}{4\pi} \quad (16)$$

then the admittance is a simple function of the conductivity:

$$Y = \frac{I}{V} = \frac{4\pi}{\sigma} \quad (17)$$

Thus, the conductivity is simply $$\sigma = 4\pi \frac{V}{I} \quad (18)$$

and the resistivity is $$\rho = \frac{1}{\sigma} = \frac{I}{V} \frac{1}{4\pi} \quad (19)$$

As can be seen from the foregoing disclosure and mathematical analysis of the basis of operation of the system of the present invention shown in FIG. 2, a constant voltage or current in the range of 20 KHz–20 MHz is applied to terminals 37 and 38 of the coil 36 while fluid flow occupies the gap region 30. A variable capacitor 47 is placed across the terminals 37 and 38 and varied to produce a minimum current or maximum voltage condition. The varying current or voltage value with a constant input is directly indicative of the varying resistivity of the fluid.

Referring again to FIG. 2, more particularly, the output terminals 37 and 38 of the coil 36 have a variable capacitor 47 connected across them. The coil terminals 37 and 38 are connected to the output of a low input impedance constant voltage power supply 50 through a resistor 51. The power supply 50 delivers a voltage of constant magnitude having a frequency between 20 KHz and 20 MHz. The voltage developed across the resistor 51 is connected to the input of a differential amplifier 53 whose output is connected to the input of an analog-to-digital converter 54. Digitized information from the A/D converter 54 is coupled to a telemetry system 55 for transmission of the data to the surface for observation and utilization. The value of the variable capacitor 47 is adjusted to tune the circuit to resonance during calibration prior to use.

In operation constant voltage from power supply 50 is connected across coil 36 while fluid 35 flows through the core gap enclosing recess region 30. Variations in the resistivity of the fluid produce corresponding variations in the current flowing through the resistor 51 and a changing voltage at the input to the differential amplifier 53. The amplified analog voltage output of the amplifier 53 is converted to digital format in the A/D converter 54 and sent to the surface for use via telemetry system 55.

It is thus believed that the operation and construction of the present invention will be apparent from the foregoing description. While the method and apparatus shown and described have been characterized as being preferred, it will be obvious that various changes and modifications may be made therein without departing from the spirit and scope of the invention as defined in the following claims.

We claim:

1. Apparatus for measuring the electrical resistivity of fluid within a borehole comprising:
   a. a housing disposable along a pipe string in such a borehole;
   b. said housing being formed with a sensor region in the outer surface thereof, said sensor region having a pair of generally opposed wall end portions and being adapted to be substantially and continuously filled by fluid flowing along the outer surface of the housing;
   c. a high permeability magnetic core having a pair of opposed ends forming a gap region therebetween, said core being positioned within said housing and having its respective ends positioned adjacent to said opposed wall portions of said sensor region to position said sensor region within said gap of said core;
   d. means for producing an alternating, electromagnetic flux field of a substantially constant magnitude in said core and said gap region to induce eddy currents in fluid in said sensor region; and
   e. means for generating a signal corresponding to fluctuations in the electromagnetic flux field in said core to measure the electrical resistivity of fluid flowing along the outer surface of said housing.

2. Apparatus as set forth in claim 1 wherein said electromagnetic flux producing means includes a conductive coil wrapped around said core and a signal generator having a constant output signal connected to said coil and comprising a signal generation circuit.

3. Apparatus as set forth in claim 2 further comprising a capacitor connected across said coil for tuning the circuit to resonance.

4. Apparatus as set forth in claim 2 wherein said means for generating a signal includes means for measuring the current flow in said coil due to back voltage in said core produced by eddy currents in fluid in said sensor region.

5. Apparatus as set forth in claim 1 wherein said end surfaces of said core form said opposed planar walls of said sensor region and are in direct contact with said fluid flowing through said sensor region.

6. Apparatus as set forth in claim 1 further comprising means for communicating said signal indicative of electrical resistivity of said fluid to the surface of the borehole.

7. Apparatus as set forth in claim 1 wherein said housing comprises a pipe section having means for coupling to adjacent pipe within said pipe string.

8. Apparatus as set forth in claim 7 wherein said housing is coupled to said pipe in a drill string in a position above a drill bit and in the general proximity thereof for measuring said electrical resistivity of fluid around said drill bit.

9. Apparatus as set forth in claim 1 wherein said sensor region of said housing includes a recessed region formed within the outer surface of said housing wherein fluid will flow therein and within said gap of said core.

10. Apparatus as set forth in claim 9 wherein said opposed wall portions of said sensor region are planar wall areas.

11. Apparatus as set forth in claim 1 wherein said opposed planar walls of said housing are formed at an angle one to the other.

12. Apparatus as set forth in claim 9 wherein said opposed planar walls of said housing are formed generally orthogonal one to the other for defining a generally arcuate electromagnetic flux field.

13. Apparatus for measuring the electrical resistivity of fluid within a borehole comprising:
    a. a drill sub adapted for location within a drill pipe string of a borehole drilling rig;
    b. a recess region formed in the outer surface of said sub, said recess region having a pair of generally opposed planar walls and being adapted to be substantially and continuously filled by fluid flowing along the outer surface of the sub and returning to the surface;
    c. a high permeability magnetic core having a pair of opposed ends forming a gap region therebetween, said core being positioned within said sub and having the respective ends positioned adjacent to said opposed planar walls of said recess region to position said recess region within said gap of said core;
    d. means for producing an alternating, electromagnetic flux field of a substantially constant magnitude in said core and said gap region to induce eddy currents in fluid flowing through said recess region in the outer surface of the sub; and
    e. means for generating a signal proportional to the fluctuations in the electromagnetic flux field in said core to measure the electrical conductivity of fluid flowing along the outer surface of said sub.

14. Apparatus as set forth in claim 13 wherein said electromagnetic flux producing means includes a conductive coil wrapped around said core and a signal generator having a constant output signal connected to said coil and comprising a signal generation circuit.

15. Apparatus as set forth in claim 14 further comprising a capacitor connected across said coil for tuning said circuit to resonance.

16. Apparatus as set forth in claim 14 wherein said proportional signal generating means includes means for measuring the current flow in said coil due to back voltage in said core produced by eddy currents in fluid in said recess region.

17. Apparatus as set forth in claim 13 wherein said end surfaces of said core form said opposed planar walls of said recess region and are in direct contact with said fluid flowing through said recess region.

18. Apparatus as set forth in claim 13 wherein said opposed planar walls of said recess are formed at an angle one to the other.

19. Apparatus as set forth in claim 18 wherein said opposed planar walls of said recess are formed generally orthogonal one to the other for defining a generally arcuate electromagnetic flux field.

20. Apparatus as set forth in claim 13 wherein said sub is coupled to said drill pipe in a position above said drill bit and in the general proximity thereof for measuring said electrical resistivity of said fluid around said drill bit.

21. A method for measuring the electrical resistivity of drilling fluids flowing within an operating borehole and relative to a drill bit, said method comprising the steps of:
    a. providing a sub having a recess region formed in the outer surface thereof and adapted for coupling to a drill pipe string of a borehole drilling rig, said recess region of said sub comprising a pair of opposed, planar walls;
    b. positioning said sub in said drill string and within said borehole relative to said drill bit;
    c. flowing fluids within said recess of said sub for measuring the electrical resistivity of said fluids;
    d. generating an alternating, electromagnetic flux field of a substantially constant magnitude within said recess region; and
    e. producing an output signal in response to the variations in the flux field produced by eddy current flow in said drilling fluids, said output signal being indicative of the resistivity of the drilling fluids in the recess region.

22. A method as set forth in claim 21 wherein said recess region includes a pair of opposed planar walls and is adapted to be substantially and continuously filled by drilling fluids flowing along the outer surface of the sub and returning to the surface, and wherein said flux field generating step includes:
    a. providing a high permeability magnetic core having a pair of opposed ends forming a gap region therebetween;
    b. positioning said core within said sub with the respective ends of said core positioned adjacent to said opposed planar walls of said recess region; and
    c. producing an alternating, electromagnetic flux field in said core to induce eddy currents in the drilling fluids flowing through said gap region.

23. A method as set forth in claim 22 wherein said step of producing a flux field in said core includes the steps of providing a conductive coil around said core and generating a signal across said coil with a signal generation circuit.

24. A method as set forth in claim 23 wherein said step of providing a coil around said core includes the step of applying a capacitance across said coil to tune said circuit to resonance.

25. A method as set forth in claim 23 wherein said step of producing an output signal responsive to flux field variations includes the steps of measuring the current flow in said coil due to back voltage in said core produced by eddy currents in said fluids in said gap region.

* * * * *

UNITED STATES PATENT AND TRADEMARK OFFICE
CERTIFICATE OF CORRECTION

PATENT NO. : 4,536,713
DATED : August 20, 1985
INVENTOR(S) : Mark H. Davis; Richard A. Meador; Macmillan M. Wisler It is certified that error appears in the above—identified patent and that said Letters Patent is hereby corrected as shown below:

In Column 6, line 3, delete "$e^{i\omega t}$" and insert therefor --$e^{-i\omega t}$--.

In Column 6, line 20, delete "$\nabla \cdot E$" and insert therefor --$\nabla \times E$--.

In Column 6, line 22, delete "$\nabla \cdot \frac{J}{\sigma}$" and insert therefor --$\nabla \times \frac{J}{\sigma}$--.

Signed and Sealed this

Eleventh Day of February 1986

[SEAL]

Attest:

DONALD J. QUIGG

Attesting Officer

Commissioner of Patents and Trademarks